United States Patent
Kuenen et al.

(10) Patent No.: US 11,766,297 B2
(45) Date of Patent: Sep. 26, 2023

(54) APPARATUS AND METHOD FOR DETECTING AN INTERVENTIONAL TOOL

(71) Applicant: KONINKLIJKE PHILIPS N.V., Eindhoven (NL)

(72) Inventors: Maarten Petrus Joseph Kuenen, Veldhoven (NL); Nenad Mihajlovic, Eindhoven (NL); Arash Pourtaherian, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 876 days.

(21) Appl. No.: 16/333,884

(22) PCT Filed: Sep. 18, 2017

(86) PCT No.: PCT/EP2017/073425
§ 371 (c)(1),
(2) Date: Mar. 15, 2019

(87) PCT Pub. No.: WO2018/050885
PCT Pub. Date: Mar. 22, 2018

(65) Prior Publication Data
US 2019/0201110 A1    Jul. 4, 2019

Related U.S. Application Data

(60) Provisional application No. 62/395,597, filed on Sep. 16, 2016.

(30) Foreign Application Priority Data

Jun. 12, 2017  (EP) .................................. 17175503

(51) Int. Cl.
*A61B 34/20*  (2016.01)
*A61B 8/08*   (2006.01)
(Continued)

(52) U.S. Cl.
CPC ............ *A61B 34/20* (2016.02); *A61B 8/0841* (2013.01); *A61B 8/145* (2013.01); *A61B 8/4461* (2013.01);
(Continued)

(58) Field of Classification Search
CPC ....... A61B 34/20; A61B 8/483; A61B 8/4461; A61B 8/145; A61B 8/0841; A61B 8/466;
(Continued)

(56) References Cited

U.S. PATENT DOCUMENTS 10,292,684 B2 *   5/2019  Okazaki ................ A61B 8/483
2012/0253181 A1 * 10/2012  Okamura ............. A61B 8/5238
                                                    600/424
(Continued)

FOREIGN PATENT DOCUMENTS

CN    102920476 A    2/2013
WO    2011107404 A1  9/2011
(Continued)

OTHER PUBLICATIONS

Pourtaherian, A. et al., "Gabor-Based Needle Detection and Tracking in Three-Dimensional Ultrasound Data Volumes", Eindhoven University of Technology, The Netherlands, 2014.

*Primary Examiner* — Boniface Ngathi N
*Assistant Examiner* — Zainab Mohammed Aldarraji

(57) ABSTRACT

An apparatus that detects a tip of an interventional tool based on at least two ultrasound images reconstructed for different beam steering angles within a volumetric region that includes the tool. The apparatus includes an image processor. The image processor includes a tip detection module used to perform a tip tool detection procedure. The tip tool detection procedure involves identifying shadow regions of
(Continued)

the tool in the at least two ultrasound images and determining the position of the tip of the tool within the volumetric region.

21 Claims, 8 Drawing Sheets

(51) Int. Cl.
| | |
|---|---|
| A61B 8/00 | (2006.01) |
| G01S 15/89 | (2006.01) |
| G06T 7/00 | (2017.01) |
| A61B 8/14 | (2006.01) |
| G06T 5/50 | (2006.01) |
| G06T 7/73 | (2017.01) |
| G10K 11/34 | (2006.01) |
| A61B 17/34 | (2006.01) |
| A61B 90/00 | (2016.01) |

(52) U.S. Cl.
CPC .............. *A61B 8/466* (2013.01); *A61B 8/483* (2013.01); *G01S 15/8915* (2013.01); *G01S 15/8993* (2013.01); *G01S 15/8995* (2013.01); *G06T 5/50* (2013.01); *G06T 7/0012* (2013.01); *G06T 7/0014* (2013.01); *G06T 7/73* (2017.01); *G10K 11/34* (2013.01); *A61B 2017/3413* (2013.01); *A61B 2034/2063* (2016.02); *A61B 2034/2065* (2016.02); *A61B 2090/378* (2016.02); *G06T 2207/10136* (2013.01); *G06T 2207/20224* (2013.01)

(58) Field of Classification Search
CPC .... A61B 2034/2063; A61B 2034/2065; A61B 2017/3413; A61B 2090/378; G06T 5/50; G06T 7/0014; G06T 7/73; G06T 7/0012; G06T 2207/10136; G06T 2207/20224; G06T 2207/30021; G06T 2207/10132; G01S 15/8995; G01S 15/8915; G01S 15/8993; G10K 11/34
See application file for complete search history.

(56) References Cited

U.S. PATENT DOCUMENTS

| | | | |
|---|---|---|---|
| 2012/0321154 A1* | 12/2012 | Korsten | A61B 8/0841 382/128 |
| 2016/0199025 A1* | 7/2016 | Takeda | A61B 8/5207 600/424 |

FOREIGN PATENT DOCUMENTS

| | | |
|---|---|---|
| WO | 2014174305 A2 | 10/2014 |
| WO | 2017097682 A1 | 6/2017 |

* cited by examiner

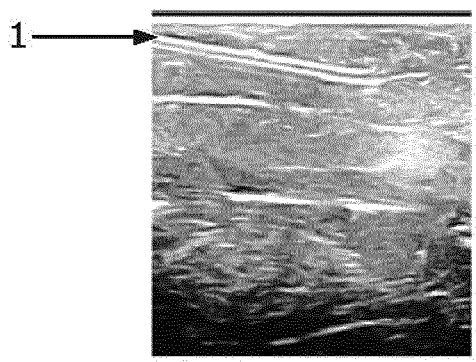
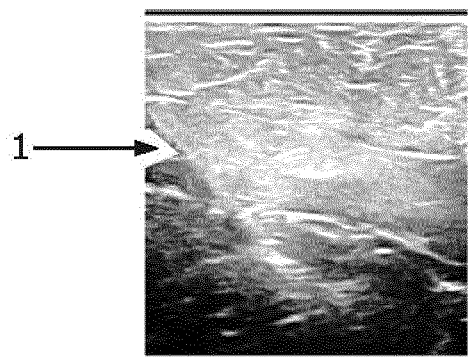
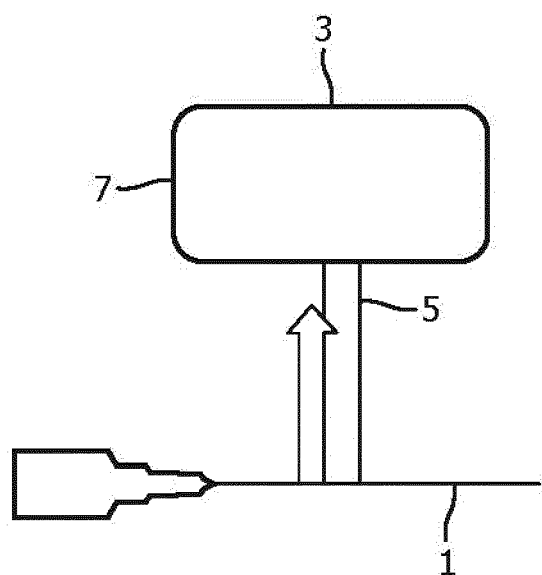
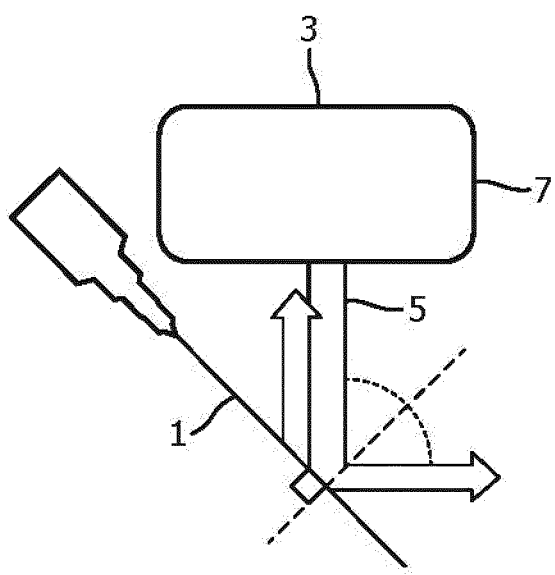
FIG. 1A
FIG. 1B

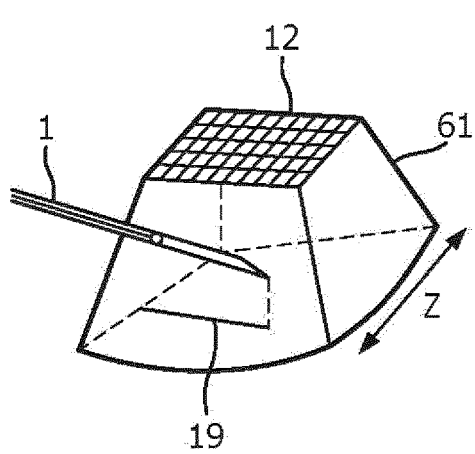
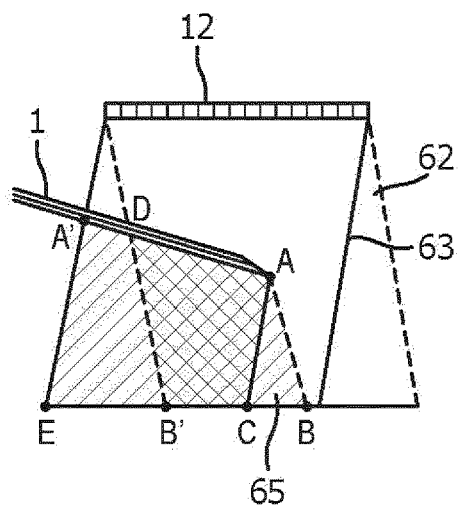
FIG. 3
FIG. 4
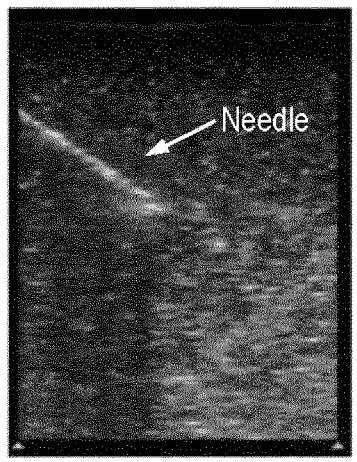
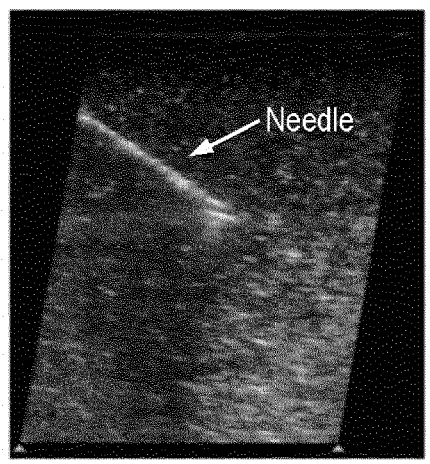
(a)     (b)
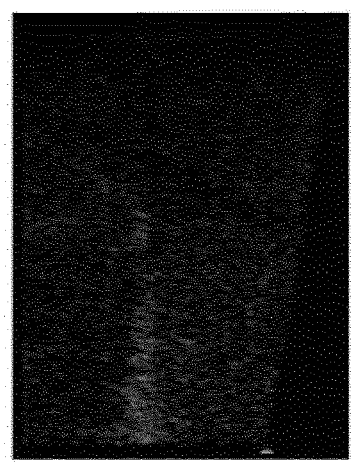
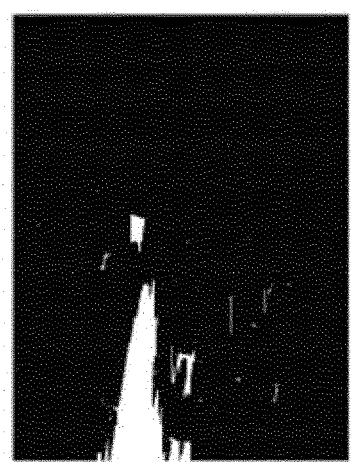
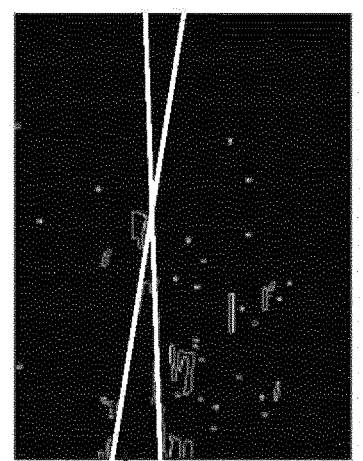
(c)     (d)     (e)
FIG. 5

APPARATUS AND METHOD FOR DETECTING AN INTERVENTIONAL TOOL

CROSS-REFERENCE TO PRIOR APPLICATIONS

This application is the U.S. National Phase application under 35 U.S.C. § 371 of International Application No. PCT/EP2017/073425, filed on 18 Sep. 2017, which claims the benefit under 35 U.S.C. § 119(e) of U.S. Provisional Patent Application No. 62/395,597, filed on 16 Sep. 2016 and European Patent Application No. 17175503.6, filed on 12 Jun. 2017. These applications are hereby incorporated by reference herein.

FIELD OF THE INVENTION

The present invention relates to an apparatus and method for detecting a tool including a tip of the tool, and in particular to an apparatus and method for imaging an interventional tool using images obtained by ultrasound imaging.

BACKGROUND OF THE INVENTION

Ultrasound imaging is one of the most popular imaging systems for tool guidance applications. Ultrasound imaging may be used to image tools such as needles, laparoscopes, stents, and radioactive seeds used for brachytherapy. For example, ultrasound imaging may be used for needle guidance in anesthesiology, tissue ablation or for biopsy guidance, since needles are used to take tissue samples, and to deliver medicine or electrical energy to the targeted tissue inside a patient's body. During these procedures, visualization of the needle and its tip is very important in order to minimize risk to the patient and improve health outcomes.

Typically, 2D ultrasound guidance is used to visualize an interventional tool while a procedure is being conducted. However, this mode of imaging has a number of drawbacks. In particular, 2D imaging has a limited field of view; after a successful alignment and localization of the tool in the ultrasound image and while moving the tool or assessing the target, any undesired hand motion of the person conducting the procedure may cause misalignment of the tool and the ultrasound transducer such that parts of the tool are excluded from the ultrasound image. This may lead to incorrect placement of the tool. Furthermore, during the procedure, the focus of the operator may be diverted from treatment, as they may be distracted by searching for the tool in the ultrasound image.

External tool tracking systems also have a number of disadvantages, since they require additional equipment, which adds to the cost of the ultrasound imaging system. Further, a specialized needle comprising additional sensors is required. Limiting the physician to the use of a specialized needle will likely add to the cost of the procedure.

Tool detection techniques have been proposed in 3D ultrasound based on directionally sensitive spectral transformations, which are shown to be more robust to noise and can detect the needle in challenging situations (for example, A. Pourtaherian, et al., "*Gabor-Based Needle Detection and Tracking in Three-Dimensional Ultrasound Data Volumes,*" in Proc. IEEE ICIP, pp 3602-6, 2014). Further, most of the detection techniques derive location of a top of the tool within the ultrasound image based on the needle's axis identification, which is not always possible with higher precision.

Nevertheless, these proposals do not enable detection of a tool when the insertion angle of the tool (the angle between the incident ultrasound radiation and the tool) is large. In these cases, incident beams are reflected at large angles and, as a consequence, are not detected by the ultrasound imaging system. Accordingly, the tool is almost invisible in the acquired data set.

FIGS. 1A and 1B show a typical ultrasound imaging system and illustrate the insertion angle of a tool 1, together with a corresponding ultrasound image of the tool 1. An ultrasound apparatus 3, comprising an ultrasound emitter (ultrasound array) and an image sensor, is arranged to emit ultrasound waves 5 towards a subject. They form incident ultrasound radiation to the subject. The ultrasound apparatus 3 acquires a dataset which, based on the reflected ultrasound radiation, is used to image the tool 1. The emitted ultrasound radiation in this example propagates in a direction substantially perpendicular to the emission surface 7 of the ultrasound array of the ultrasound apparatus 3.

The tool 1 is inserted at an angle to the emission surface 7 of the ultrasound array, which in this illustration is assumed to coincide with the surface of the ultrasound apparatus 3. The insertion angle of the tool is the angle between the emission surface 7 of the ultrasound apparatus 3 and the tool 1, wherein the emission surface of the ultrasound array is a plane perpendicular to the transmission direction of the incident ultrasound radiation 5.

In FIG. 1A, the tool is shown at a small insertion angle; the tool is arranged substantially parallel to the emission surface 7 of the ultrasound array. In this case, the insertion angle of the tool 1 is about 0°. The ultrasound radiation 5 is reflected by a surface of the tool 1, and propagates back towards the ultrasound array, where it is detected by the image sensor (ultrasound transducers comprised in the ultrasound array). Since the tool strongly reflects the incident ultrasound radiation, it appears as a bright region in the ultrasound image data.

In FIG. 1B, the tool 1 and ultrasound apparatus 3 are provided in a different arrangement, in which the insertion angle of the tool 1 is large. In this case, the angle between the emission surface 7 of the ultrasound array and the tool 1 is about 45°. The ultrasound radiation 5 propagates towards the tool 1 and is incident on a reflective surface of the tool 1. Some of the ultrasound radiation is reflected at a large angle, causing it to be directed away from the ultrasound array. Consequently, the tool 1 is almost invisible in the ultrasound image produced by the ultrasound apparatus 3. It can be also appreciated that as the tip of the tool gets further away from the surface of the ultrasound array during the tool's advancements in the tissue the chance of the reflected ultrasound radiation to be directed away from the ultrasound array increases.

There is therefore a need for an apparatus and method for detecting a tool as well as its tip with improved 2D or 3D ultrasound imaging technique even when the tool is inserted at a large angle with respect to the emission surface of the ultrasound apparatus.

SUMMARY OF THE INVENTION

The invention is defined by the claims.

In one aspect of the present invention there is provided an apparatus for detecting a location of a tool including a tip of the tool comprising:

an image processor (15) adapted to receive from an ultrasound array an ultrasound image data of the volumetric region, said image processor comprising:

a tip tool detection module (17) configured to
reconstruct from the ultrasound image data a first ultrasound image having a first tool shadow region, wherein the first ultrasound image corresponds to a first steering angle of an ultrasound beam with respect to a surface of the ultrasound array, and a second ultrasound image having a second tool shadow region, wherein the second ultrasound image corresponds to a second steering angle of the ultrasound beam being different from the first steering angle;
identify a differential shadow region within the volumetric region based on a relative difference between the first and the second shadow region; and
determine based on the differential shadow region the location of the tip of the tool.

This embodiment is based on the idea that ultrasound image data acquired with ultrasound beams steered at different angles (also known as insonification angle) with respect to the emitting surface of an ultrasound array provide ultrasound images corresponding to different steering angles with respect to the volumetric region and accordingly to a main axis of the interventional tool. Since each ultrasound image is formed by the ultrasound beams (radiation) directed towards the tool under a different angle, a shadow region of the tool within each ultrasound image would be different depending on the incident angle between the beams and the main axis of the tool. The image processor of the apparatus is arranged to process the ultrasound data comprising different steering angles and derive from said data at least one differential shadow region based on a relative difference between two different shadow regions observed in different image frames. Position and area of each shadow region within a corresponding ultrasound image reconstructed from the ultrasound data is determined by the steering angle of said image. Since the ultrasound data is acquired for the same volumetric region comprising the same anatomy, the two reconstructed ultrasound images would substantially differ in their shadow regions. Therefore, the image processor is further arranged to analyze the relative differences in the shadow regions of two different reconstructed images and to derive the differential shadow region corresponding to the region within the volumetric region, wherein the shadow region of the tool within one image is different from the shadow region of the tool within another image. Based on the identified location of differential shadow region within the volumetric region the image processor can determine a location of the tool within the volumetric region with a high precision independent on the insertion angle of the tool. This embodiment can be applied in both two dimensional (2D) and three dimensional (3D) imaging. In this context the reconstructed ultrasound images may originate either from 2D or 3D ultrasound image.

In another aspect of the invention the tip tool detection module is further configured to
reconstruct a third ultrasound image having a third tool shadow region, wherein the third ultrasound image corresponds to a third steering angle of the ultrasound beam being different from the second steering angle,
identify a second differential shadow region within the volumetric region based on the relative difference between the third shadow region and either of the first and the second shadow regions; and
correlate the first differential shadow regions with the second differential shadow region, wherein a further determination of the location of the tip of the tool is based on the correlation of the differential shadow regions.

The invention allows to further improve the precision of the tool's location detection by comparing different differential shadow regions derived from two different pairs of the reconstructed ultrasound image. The correlation of these regions with each other, namely region parameters such as area, size and its location within a respective reconstructed ultrasound image, and with the steering angles of corresponding images wherefrom these regions were identified allows the image processor to determine the locations of the tool within the volumetric region with even better precision.

In accordance with another aspect of the invention the tip tool detection module is arranged to identify the differential shadow region in a subtracted image obtained by subtracting intensities of the respective pixels from the first and the second ultrasound images.

This embodiment is based on that non-shadow image areas outside of shadow regions would comprise pixels with similar intensity (apart from different speckle patterns) to pixels from non-shadow areas in other ultrasound images reconstructed for the same volumetric region. An area, wherein all reconstructed ultrasound images have spatially coinciding shadow regions would also have pixels with similar characteristics. However, in the area where there is a shadow region present under the first angle and no shadow region present under the second angle, there is a distinguishing difference in the intensity of the pixels forming the reconstructed images. Therefore, subtracting the intensity of the respective pixels from different ultrasound images in a common coordinate system (spatially aligned ultrasound images) gives a subtracted image, wherein the differential shadow region may be easily identified based on its distinguished intensity.

In another embodiment the received ultrasound image data may comprise a 3D ultrasound image data of the volumetric region, wherein the first ultrasound image, the second ultrasound image and the third ultrasound image belong to a plurality of image planes forming a 3D ultrasound image of the volumetric region.

In 3D ultrasound imaging, a 3D ultrasound imaging apparatus is arranged to control the ultrasound array to emit ultrasound radiation (in other words steer beams) towards a subject and to detect radiation reflected by the subject to produce a 3D ultrasound volume data set which represents a 3D volume of the subject. In this way, the 3D imaging apparatus produces an image of the 3D volume. Based on the acquired 3D ultrasound image data the image processor is arranged to reconstruct a 3D ultrasound image comprising a plurality of image planes. The tip tool detection module may be further arranged to select from said plurality of planes at least two image planes corresponding to different steering angles, wherein each of the planes includes a tool shadow region. Therefore, by acquiring one 3D ultrasound image the tip of the tool can be detected, thereby simplifying an interventional workflow.

In yet another embodiment the tip tool detection module is further configured to determine the location of a tool plane section within the 3D ultrasound image data based on the determined location of the tip of the tool, wherein the tool plane section represents a plane within a 3D image of the volumetric region in which the entire length of the tool is present The image processor is adapted to process the 3D ultrasound image data to determine which plane of the 3D image represents a plane of the 3D volume that includes the entire length of the tool, including the tip of the tool. This plane is called the tool plane section. By detecting the position of the tool plane section, it is possible to visualize the long-axis view of the tool. The tip tool detection module locates the tool plane section based on a region of the 3D ultrasound data set that represents a shadow of the tool. In this way, the location of the tool can be detected even when the insertion angle of the tool is large since a shadow of the tool is identifiable regardless of the insertion angle. In addition, other views of the tool can be determined with respect to the tool plane section. For example, a plane including a short-axis of the tool can be identified since it is a plane substantially perpendicular to the tool plane section and located at the position of the tip of the tool. Further, since the image processor processes a typical 3D ultrasound image to determine the position of the tool plane section, the apparatus can be incorporated into a typical 3D ultrasound imaging system without requiring modification of any of the other elements of the system.

In a further aspect of the invention the tip tool detection module is further configured to identify a plurality of tool shadow regions by detecting dark regions present in the plurality of planar sections and determining whether the dark regions correspond to a shadow of the tool, wherein the first, the second and the third shadow regions belong to the plurality of tool shadow regions.

The tool shadow region is a dark region that corresponds to a shadow of the tool. The tip tool detection module may analyze the detected dark regions in at least one of the planar sections to determine whether the dark region is likely to represent a shadow of the tool, for example by examining the size, width and/or shape of the dark region and comparing it to an expected size, width and/or shape of the shadow of the tool. The tip tool detection module may calculate the position of a planar section within the 3D ultrasound data that includes the entire length of the tool or the tip of the tool that is present in the volumetric region, based on the position of the tool shadow region. This section of the 3D volume data is the "tool plane section".

The apparatus may further comprise a second tool detection module which is configured to perform a second tool detection procedure comprising:

detecting the tool based on a representation of the tool in the ultrasound image, preferably using an intensity and/or frequency based algorithm.

At a shallow insertion angle, the tool is highly visible in the reconstructed ultrasound image and therefore the tool can be directly identified from said image. The tool strongly reflects incident ultrasound radiation towards the image sensor and therefore the position of tool is represented in the ultrasound image as a bright region, which can be detected using an appropriate algorithm. By providing the function of tool detection at shallow angles as well as steep angles, the apparatus can be used to detect tools over a range of insertion angles and is therefore suitable for many different applications.

This second tool detection procedure is suitable for identifying the position of the tool when the angle between the tool and the emitting surface of the ultrasound array is a small angle, so that the tool can be directly identified from the ultrasound image data. The range of insertion angles over which the tool is visible enough to detect directly will depend on the exact arrangement of the 3D imaging apparatus. However, in a typical arrangement the tool is unlikely to be visible at an insertion angle greater than 30°.

In another embodiment the ultrasound image data comprise a plurality of 3D ultrasound images, and wherein each of the first ultrasound image, the second ultrasound image and the third ultrasound image is reconstructed from a different 3D ultrasound image from said plurality.

In this embodiment the image processor is adapted to receive from the ultrasound array image data comprising the plurality of 3D ultrasound images, wherein the tip tool detection module is configured to reconstruct 3D ultrasound images of the volumetric region, thereby performing the identification of the differential shadow region in three dimensions. By receiving data for at least two 3D ultrasound images acquired at different beam steering angles with respect to the surface of the array, the tip tool detection module allows to determine based on the differential shadow region, which is in this embodiment is 3D region, the location of the tip of the tool. This way a more precise the tip tool detection may be achieved.

In an alternative embodiment the ultrasound image data may comprise a plurality of 2D ultrasound image planes, and wherein each of the first ultrasound image, the second ultrasound image and the third ultrasound image is reconstructed from a different 2D ultrasound image from said plurality.

The invention can be practiced for the plurality of 2D ultrasound image data. In the preferred implementation at least one of the images comprises the entire length of the tool thereby providing a more distinguished shadow region for processing.

An embodiment the apparatus for detecting the location of the tool including the tip of the tool may be combined with an ultrasound array arranged to steer the ultrasound beam towards the volumetric region and provide the ultrasound image data to the image processor.

In this embodiment the apparatus can be incorporated into an external device suitable to perform the functions of the image processor, wherein the ultrasound array coupled to said device, would be used to acquire ultrasound image data.

The apparatus may further comprise a display unit for displaying an ultrasound image, wherein the image processor is configured to communicate an image of the tip of the tool to the display unit. Once the location of the tip of the tool plane is by the image processor, it sends an image of the tip (the tool) to the display unit. In this way, the tool can be visualized and used for guidance.

According to an aspect of the invention, there is provided a method for detecting a tool including a tip of the tool in a volumetric region, comprising:

obtaining an ultrasound image data of the volumetric region;

reconstructing from the ultrasound image data a first ultrasound image having a first tool shadow region, wherein the first ultrasound image corresponds to a first steering angle of an ultrasound beam with respect to a surface of the ultrasound array, and a second ultrasound image having a second tool shadow region, wherein the second ultrasound image corresponds to a second steering angle of the ultrasound beam being different from the first steering angle;

identifying a differential shadow region within the volumetric region based on a relative difference between the first and the second shadow region; and determining based on the differential shadow region the location of the tip of the tool.

By performing this method, a tip of the advancing tool within the volumetric can be quickly identified, enabling rapid visualization of the tool to an operator. Also, the method is less sensitive to noise and therefore provides a reliable way to detect the location of the tool in a variety of situations. Further, the method can be used to detect the tool in high noise environments. The method is concerned with processing an ultrasound image and is performed without requiring any input from a medical professional.

The invention also provides a computer program comprising code means adapted to perform the method defined above when said program is run on a computer.

By providing a computer program the functionality of an existing image processor can be altered to detect a tool and locate a tool plane section, without altering any of the typical existing equipment used for 3D ultrasound imaging.

BRIEF DESCRIPTION OF THE DRAWINGS

FIG. 1A shows an ultrasound imaging apparatus with a tool disposed at a small insertion angle of an interventional tool;

FIG. 1B shows an ultrasound imaging apparatus with a tool disposed at a large insertion angle of an interventional tool;

FIG. 3 illustrates a 3D field of view of a volumetric region comprising an interventional tool;

FIG. 4 illustrates an exemplary implementation of the present invention;

FIG. 5A to E illustrate a practical application of the present invention;

DETAILED DESCRIPTION OF THE EMBODIMENTS

Figure 2:
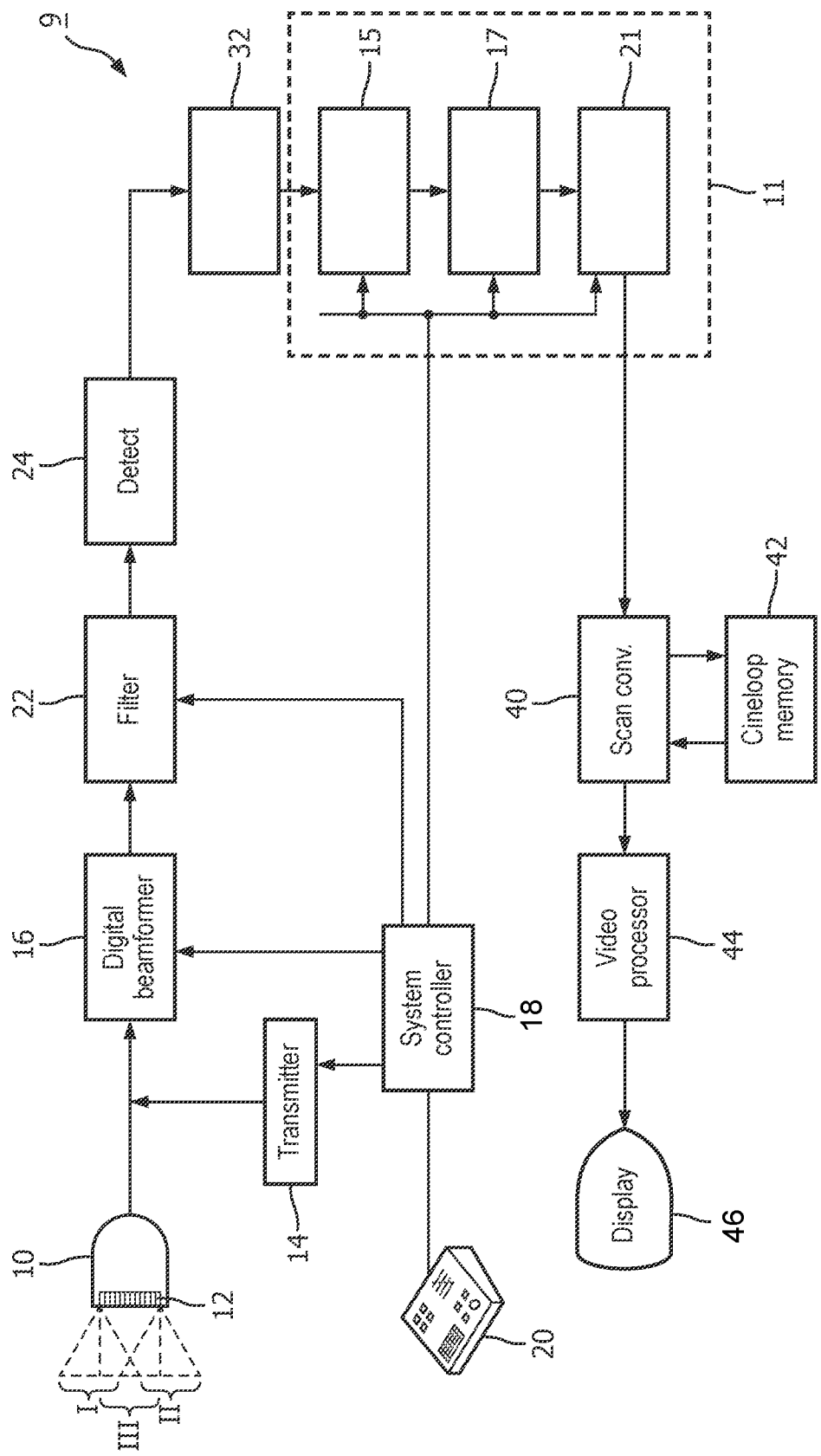
FIG. 2 illustrates in block diagram form an ultrasonic guidance imaging system according to an aspect of the present invention.

The apparatus of the present invention can be used either with 2D or 3D ultrasound imaging systems and probes. FIG. 2 shows a schematic block diagram of the ultrasound imaging system 9, which can be used in a combination with an apparatus 11 of the present invention. The ultrasound imaging system 9 has a probe 10 including an ultrasound transducer array 12 arranged to steer (transmit) ultrasound beams at different angles denoted by the dashed rectangle and parallelograms over a volumetric region. In this example, three groups of scanlines forming a plurality of ultrasound images are indicated in the drawing, labeled I, II and III with each group being steered at a different angle relative to the probe or emitting surface of the ultrasound transducer array 12. These ultrasound image data can be acquired using either a mechanically steered array or by means of electronic ultrasound beam steering. The transmission of the beams is controlled by a transmitter 14 which controls the phasing and time of actuation of each of the elements of the array transducer so as to transmit each beam from a predetermined origin along the array and at a predetermined angle.

Figure 6A:
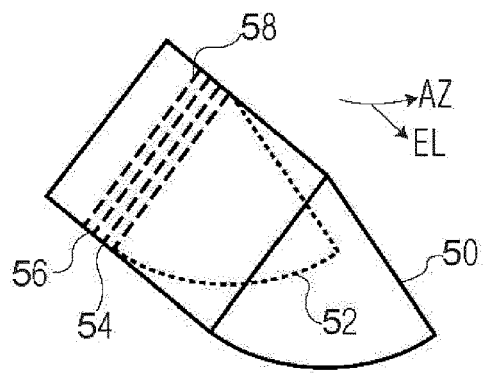
FIG. 6A illustrates a plurality of sector planes acquired in the elevational direction.
Figure 6B:
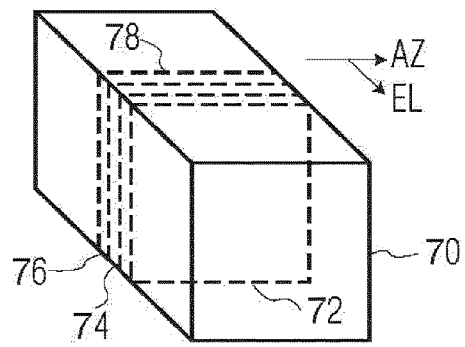
FIG. 6B illustrates a plurality of rectilinear slices acquired in the elevational direction.
Figure 6D:
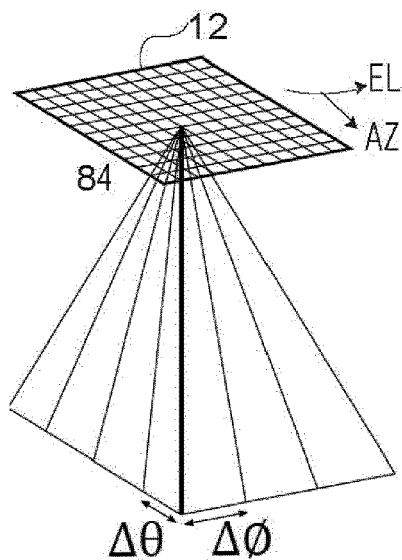
FIG. 6D illustrates a plurality of slices which are at different angular increments in the elevational as well as in the azimuthal direction.
Figure 6C:
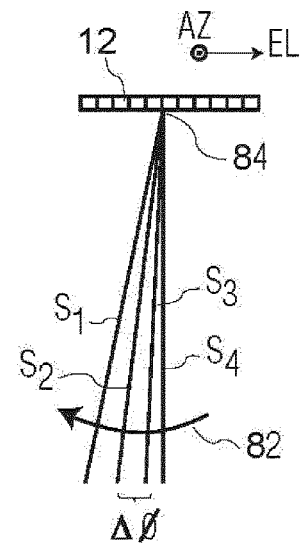
FIG. 6C illustrates a plurality of slices which are at different angular increments in the elevational direction.

It shall be understood that the application of the present invention is not limited to a specific ultrasound imaging method such as focused beam imaging, divergent or plane wave imaging, etc. For example, in FIG. 6A a volumetric region, wherein a location of a tool including a tip of the tool can be detected, is shown in perspective. In this example the volumetric region is sector-shaped and contains a plurality of planar sector-shaped areas which are referred to herein volume slices. Four slices 52-56 are illustrated in this example. The slices are oriented parallel to each other in the elevation direction with their azimuth and elevation dimensions indicated to the right of the drawing. Each slice may be scanned by the ultrasound transducer array 12 located above the volumetric region by transmitting s successive scanlines across a slice 12-16 in the azimuth direction and progressing from slice to slice in the elevation direction. FIG. 6B illustrates a rectilinear volumetric region, which also includes a plurality of slices oriented in parallel in the elevation direction. Four such slices 72-78 are shown in the drawing. These slices may be scanned in the same manner as the slices of FIG. 6B by the transducer array located above the volumetric region. In this example the slices are scanned by parallel scanlines in the azimuth direction rather than by angularly incremented scanlines from a common origin as is the case in the example of FIG. 6A. FIG. 6C provides another example of slices of the volumetric region. These slices are of a pyramidal volumetric region with an apex 84 at the top of the volume. In this example four sector-shaped slices S1-S4 are shown in an "edge-on" view. That is, the elevation direction of the slices is indicated by the arrow 82, and the azimuth direction is into the plane of the drawing. The azimuth and elevation directions with respect to the array are shown above the transducer array. In this example neighboring elevation slices are separated by an angular increment Δø. FIG. 6D illustrates a manner in which a plurality of slices can be acquired at different angular increments in the elevational direction (indicated by the angular increment Δø) as well as in the azimuthal direction (indicated by an angular increment Δø, wherein the apex of the volumetric region is indicated by 84.

Referring back to FIG. 2, the echoes returned from along each scanline are received by elements (transducers) of the array, digitized as by analog to digital conversion, and coupled to a digital beamformer 16. The digital beamformer delays and sums the echoes from the array elements to form a sequence of focused, coherent digital echo samples along each scanline. The transmitter 14 and digital beamformer 16 are operated under control of a system controller 18, which in turn is responsive to the settings of controls on a user interface 20 operated by a user of the ultrasound system in combination with the apparatus of the present invention. The system controller controls the transmitter to transmit the desired number of scanline groups at the desired angles, transmit energies and frequencies. The system controller also controls the digital beamformer to properly delay and combine the received echo signals for the apertures and image depths used. The scanline echo signals are filtered by a programmable digital filter 22, which defines the band of frequencies of interest. When imaging harmonic contrast agents or performing tissue harmonic imaging the passband of the programmable digital filter 22 is set to pass harmonics of the transmit band. The filtered signals are then detected by a detector 24. In a preferred embodiment the filter and detector include multiple filters and detectors so that the received signals may be separated into multiple passbands, individually detected and recombined to reduce image speckle by frequency compounding. For B mode imaging the detector 24 will perform amplitude detection of the echo signal envelope. For Doppler imaging ensembles of echoes are assembled for each point in the image and are Doppler processed to estimate the Doppler shift or Doppler power intensity.

FIGS. 3 and 4 illustrate an application of the inventive concept in two examples. In FIG. 3 a volumetric region comprising an interventional tool 1 (e.g., a needle) being imaged with a 2D ultrasound transducer array 12 arranged to electronically steer the ultrasound beams within a field of view 61. The steering manner of a 3D ultrasound data acquisition can be realized as illustrated in FIG. 6D. The probe comprising such a 2D ultrasound transducer array 12 is arranged to provide ultrasound image data corresponding to a plurality of cross sections (slices) of the volumetric regions acquired along the elevation dimension Z and/or azimuthal dimension. Each given ultrasound slice progressively acquired in the elevation (and/or azimuthal) direction has a different inclination angle with respect to a normal vector of a surface of the ultrasound array (emitter). The plurality of these ultrasound slices can be also acquired using a 1D array, wherein the cross sections of the volumetric region are investigated by means of the mechanical movement of the array along the elevation dimension Z. The acquired ultrasound image data can be further processed by a 3D image data unit 32 in order to reconstruct a 3D ultrasound image of the volumetric region.

As illustrated in FIG. 3 the interventional tool 1 casts a shadow 19 within the field of view 61, the location of this shadow within the field of view is determined by a steering angle of the ultrasound beams used for the ultrasound data acquisition, wherein the steering angle is defined as an angle between the direction of the ultrasound beams and the normal vector to the array surface. In this figure the field of view is directly positioned below the array's emitting surface.

The ultrasound image data or the 3D ultrasound image of the volumetric region can be received by an image processor 15. The image processor 15 comprises a tip tool detection module 17 configured to reconstruct from the received ultrasound image data a first ultrasound image having a first tool shadow region, wherein the first ultrasound image corresponds to a first steering angle of an ultrasound beam with respect to a surface of the ultrasound array, and a second ultrasound image having a second tool shadow region, wherein the second ultrasound image corresponds to a second steering angle of the ultrasound beam being different from the first steering angle.

FIG. 4 illustrated a principle of the invention in 2D representation, wherein two ultrasound image planes 63 and 62 are shown. Ultrasound image plane 63 is reconstructed to correspond to a positive inclination angle with respect to the normal vector to the array and ultrasound image plane 62 is reconstructed to correspond to a negative inclination angle with respect to the normal vector. Because of different incident angles between the ultrasound beams corresponding to the respective plane and the interventional tool 1, a shadow region of this tool varies from one plane to another. Image areas without any shadow (non-shadow image areas) will have similar, apart from different speckle patterns, image parameters such as intensity. Image areas, where all images have spatially coinciding shadow regions, would also have similar characteristics. However, in the area where there is a shadow region present under the first angle and no shadow region present under the second angle there would be a distinguishing difference in image characteristic between the first and second reconstructed images. For example, in ultrasound image plane 62 a 2D cross section of the first shadow region is defined by the parallelepiped ABB'D, while in ultrasound image plane 63 the tool casts a second shadow region defined by the parallelepiped ACEA'. The two shadow regions share a spatially overlapping area defined by the parallelepiped ACB'D. Thus, by comparing both shadow region between each other and their relative position within a common coordinate system of the images it is possible to precisely determine a location of the tip of the tool. This comparison can be done based on the intensity summation performed along the scanlines of a differential shadow region 65 (ABC): along scanlines AC and AB of the differential shadow tool region, wherein shadow region of ultrasound image plane 63 is different from the shadow region of ultrasound image plane 62. This provides a one-dimensional array of summed intensities for different offset levels that will feature a jump at the desired offset. By calculation of the derivative of this summed intensity over the offset level, this jump can easily be detected. When the offset of both shadow scanlines (AC and AB) is known, the tool's tip can be found at the intersection of the two shadow scanlines.

It shall be noted that this concept may work for any intentional tool having a tip, such as a catheter or needle. This principle is also applicable for 3D ultrasound images, wherein each 3D ultrasound image will be reconstructed from 3D ultrasound image data acquired at different beam steering angles. This may be enabled by providing an ultrasound system capable of 3D ultrasound imaging, which is arranged to control steering of the field of view 61 to the side from its position shown in FIG. 3 and acquire a plurality 3D image frames for different field of view orientation within the volumetric region. The 3D image data unit 32 can also include an image memory unit. The image memory is a frame storage buffer and can be implemented as a dual port memory, which can be written to and read from simultaneously. The use of such a memory enables the new ultrasound image frames being acquired by the transducer array and beamformer to be written into one area of the memory while the data of other image frames previously stored in the memory is read out and analyzed.

In this embodiment the tip tool detection module 17 is configured to reconstruct 3D ultrasound images from received the 3D ultrasound image data, wherein the identified differential shadow region would be three-dimensional and a location of the tool's tip would be determined in a 3D space.

In another embodiment the tip tool detection module 17 may be configured to reconstruct 2D image planes from the 3D ultrasound image data. In this embodiment the first ultrasound image and the second ultrasound image would belong to a plurality of 2D image planes forming the 3D ultrasound image suitable for visualization. The tip tool detection module 17 may be arranged to identify in said plurality of planes at least two image planes corresponding to different steering angles of the ultrasound beam, wherein each of the planes includes a shadow region. In this case acquiring only one 3D ultrasound image would be sufficient for the ultrasound imaging system 9 to determine the location of the tip of the tool, thereby simplifying an interventional workflow.

In yet another implementation of the invention the tip tool detection module 17 would reconstruct the first ultrasound image plane from the 3D ultrasound image data acquired at a first ultrasound beam transmission event (a first 3D ultrasound image frame); and the first ultrasound image plane from the 3D ultrasound image data acquired at a second ultrasound beam transmission event (a second 3D ultrasound image frame). Thus, providing the two ultrasound image planes originating from two different 3D ultrasound image frames, preferably acquired at different beam steering angles.

The image processor 15 may be arranged to receive ultrasound image data in a form of a plurality of 2D ultrasound image planes, and wherein each of the first ultrasound image, the second ultrasound image and the third ultrasound image is reconstructed from a different 2D ultrasound image from said plurality. The tip tool detection module 17 may be further arranged to reconstruct those ultrasound image planes, wherein an entire length of the tool is detected, based on tool's shadow region.

Referring back to FIG. 2, wherein the apparatus 11 for detecting the location of the tip of the tool is illustrated as an optionally separate unit from the rest of the ultrasound imaging system 9. The apparatus comprises the image processor 15 adapted to receive the ultrasound image data of the volumetric region. The apparatus further includes the tip tool detection module 17 configured to perform a detection procedure involving identifying a shadow region of the tool in the ultrasound image to be reconstructed and calculating the position of the tip of tool within the volumetric region. The procedure comprise: identify a differential shadow region within the volumetric region based on the relative difference between the first and the second shadow region. This can be done by, for example, registering pixels of two different ultrasound images to the common coordinate system and subtracting pixel intensities of one image from another image, thereby forming the differential image. The tip tool detection module 17 is further arranged to analyze the differential image and detect the differential shadow region (such as ACB) located therein. Based on the location and shape of the differential shadow region within the common coordinate system the location of the tip of the tool can be determined.

The tip tool detection module 17 may be additionally configured to reconstruct a third ultrasound image having a third tool shadow region, wherein the third ultrasound image corresponds to a third steering angle of the ultrasound beam being different from the second steering angle, identify a second differential shadow region within the volumetric region based on the relative difference between the third shadow region and either of the first and the second shadow regions; and correlate the first differential shadow regions with the second differential shadow region, wherein a further determination of the location of the tip of the tool is based on the correlation of the differential shadow regions.

The invention allows to further improve the precision of the tip's location detection by comparing different differential shadow regions derived from two different pairs of the reconstructed ultrasound images. The correlation of these regions with each other, namely region parameters such as area, size and its location within the common coordinate system, and with the steering angles of the respective ultrasound images wherefrom these regions were identified allows the image processor to determine the locations of the tool within the volumetric region with even better precision The correlation can be done based on more reconstructed ultrasound images in order to provide even higher precision of the tool detection. In this next to the location of the tool's tip a main axis of said tool can be easier determined thereby enabling the apparatus 11 to estimate a trajectory of the advancing tool in the volumetric region. The tip tool detection module 17 is arranged to correlate tool shadow regions from the reconstructed 2D ultrasound images as well as from the reconstructed 3D ultrasound images, in the latter case volumetric shadow regions are compared to each other. In the present example the tip tool detection module 17 is shown as a separate unit of the apparatus 11, in alternative embodiment the tip tool detection module 17 can also be a part of the image processor 15. Further, the ultrasound images may converted in 2D or 3D ultrasound image display formats by a scan converter 40. The ultrasound images may be stored in a Cineloop® memory 42 in either estimate or display pixel form. If stored in estimate form the images may be scan converted when replayed from the Cineloop memory for display. Following scan conversion the images are processed for display by a video processor 44 and displayed on an image display 46. The ultrasound system can also provide a possibility for the user input into the tool identification process via the system controller 18 coupled to the apparatus 11.

The tip tool detection module 17 may process the ultrasound image data to detect whether the ultrasound images comprises any dark regions. The detected dark regions may include dark regions that do not relate to the tool shadow. The relative position of detected dark regions in different ultrasound images may then be analyzed to further narrow the set of dark regions to a subset which form the overall tool shadow. Therefore, the tip tool detection module may determine whether the dark regions correspond to a tool shadow based on the relative position of other detected dark regions. The set of dark regions that are most consistent with each other may be identified as tool shadow regions, which form an overall tool shadow.

FIG. 5 illustrate an example of a correlation and detection steps performed by the tip tool detection module 17. FIGS. 5A and 5B show B-mode images acquired with the inclination frame angles of 0° and 10°, respectively. The two ultrasound images subtracted from each other result in the differential B-mode image is shown in FIG. 5C, wherein a bright triangular-shaped region (similar to triangle ABC from FIG. 4) corresponds to the part of the image, where a shadow is only observed under one of the steering angles. Note, depending on the order of the two images subtraction the differential shadow region may have pixels with opposite signs of the subtracted pixel intensity. Thus, the tip detection unit may be constructed during the identification of the differential shadow region to compare the intensities of the differential image to a threshold intensity value. FIG. 5D shows the result of a post processing step on the differential image for smoothing and noise reduction, such as thresholding and morphology. In order to identify the borders of the triangular shaped region detected in the previous step, the tip tool detection module 17 can implement an edge detection algorithm by followed by a line detector such as Hough or Gabor transform, etc. Based on the shadow region, it may be possible to estimate the complete needle trajectory, and display it in the ultrasound image.

In case the image processor 15 receives the 3D ultrasound image data, the tip tool detection module 17 may be further configured to detect a location of a tool plane section within the 3D ultrasound image data. The tool plane section represents a plane within the 3D image in which the entire length of the tool is present, based on the detected tip of the tool. This then enables the tool to be visualized in the most effective way for the user of the system. The tool plane detection involves, based on the determined location of the tip of the tool, identifying the shadow of the tool in the 3D image data and calculating the position of the "tool plane section" of the 3D image in which the entire length of the tool is represented. The tool detection procedure enables rapid location of the tool plane section. In this way, the image processor is capable of efficiently detecting the tool section plane, whilst being robust to noise. By obtaining this information, rapid and accurate visualization of the tool is enabled on the image display 46.

The apparatus 11 can be incorporated into an ultrasound imaging system 9 without requiring modification of other components of the ultrasound imaging equipment. The apparatus 11 can be also sold as a separate module arranged to be implemented with portable display devices and different ultrasound probes. The apparatus 11 is configured to communicate with the ultrasound imaging system 9 or the portable display device it may be coupled to. A further advantage of the apparatus 11 is that it can be used to detect a tool over a large range of insertion angles. In a typical ultrasound guidance procedure, the tool is located by detecting a bright region of the ultrasound image which represents the tool. However, since the 3D volume is imaged by detecting reflected radiation, the tool is difficult to detect in situations where the insertion angle of the tool is large. This is because the ultrasound radiation is reflected by the tool at a large angle, and therefore is not detected by the image sensor (as illustrated by FIG. 1B). Therefore, at large insertion angles, visibility of the tool in the ultrasound image may be poor.

The image processor 15 detects the tip of the tool by identifying a differential shadow region within the volumetric region. This enables the tip of the tool to be detected, even when the tool is orientated in such a way that visibility of the tool is poor, for example between 45 degrees and 90 degrees. The visibility of a needle decreases significantly with increasing the insertion angle. Therefore, for insertion angles larger than 30°, detection of a normal needle (not special or echogenic) is very likely to fail or to be unreliable.

The image processor may be further arranged to detect the tool plane section. An outer surface of the tool strongly reflects incident ultrasound radiation and therefore most of the ultrasound radiation incident on the tool is reflected, irrespective of the orientation of the tool. Some of the incident radiation is transmitted, but the intensity is of the transmitted beams is significantly lower than that of the reflected beams. Therefore, a region of the image that represents a side of the tool opposite to the side on which ultrasound radiation is incident is relatively dark. This effect is particularly strong when the insertion angle of the tool is large since a larger proportion of the incident ultrasound beams are reflected away from the image sensor. Accordingly, next to the tip of the tool, the shadow of the tool can be detected over a wide range of insertion angles.

Figure 7:
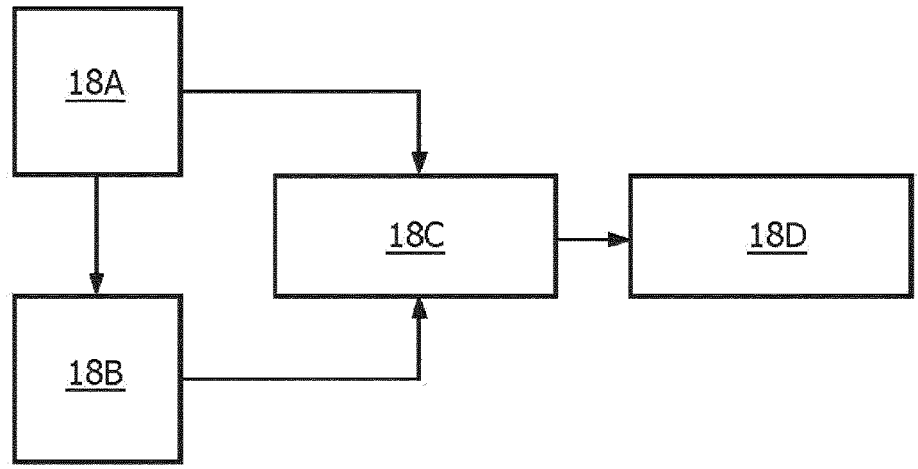
FIG. 7 illustrates a method for detecting a tool according to an example.

FIG. 7 illustrates the tool detection procedure performed by the image processor according to an example of the invention.

A tool detection procedure begins at 18A, where the location of the tip of the ultrasound tool is determined. Further, a plurality of 2D planes is reconstructed from the 3D ultrasound image data, generated by the ultrasound array. The 2D planes represent sections of the imaged 3D volume are perpendicular to the transmission direction of ultrasound radiation emitted by the ultrasound imaging system. The shadow of the tool is most visible in these planar sections of the 3D image. Therefore, using these planar sections to locate the tool enables fast and accurate identification of the tool shadow. The planar sections are obtained at different depths of the 3D image, providing a set of planar sections.

Next, at 18B, the 2D planes obtained in 18A are analyzed to detect dark regions of the 2D planes that may represent a shadow of the tool. The analyses already uses the determined tip location as an input in order to limit the number of 2D planes to be assessed. In planes beneath the needle, a shadow of the needle will appear as an ellipsoidal blob, which is relatively dark to a neighboring region of the 3D image. Therefore, after de-noising the image and performing analysis techniques such as negative thresholding, line detection or segmentation techniques, dark regions having the properties typical of the tool shadow can be identified. Further enhancement can be implemented by examining the size, width and shape of the dark regions, since the size, width and shape of the needle is known and therefore an expected size, width and shape of the shadow can be calculated. However, not all the dark regions present in the planar sections correspond to a shadow of the tool. Therefore, some of the detected dark regions do not form part of the tool shadow.

Next, at 18C, the dark regions detected at 18B are processed to identify which of the dark regions correspond to the tool shadow. By identifying at least one tool shadow region, it is possible to determine the location of a plane of the 3D image which represents the full length of the needle along a longitudinal axis of the volume. Note, that the tool shadow analyses technique disclosed herein can be applicable for both: the shadow regions detection used in the differential shadow region identification as well as for the shadow region detection used in the tool plane section.

The location of the tool section plane may be determined based on the position of a single detected tool shadow region, or multiple tool shadow regions from different 2D planes which together form a detected overall shadow.

There are different ways to process ultrasound images to identify the dark regions which are tool shadows. These tool shadow regions are a subset of the detected dark regions. To identify this subset, a random sample and consensus algorithm (RANSAC) is performed on the data set. In the RANSAC method, a fitting model is determined and elements of the dataset are checked to determine which elements are consistent with the fitting model. The tool shadow region subset is a subset of the dataset that has minimal outliers.

In one example, in order to locate the tool shadow region subset, a possible tool plane is chosen, and the number of detected dark regions in 2D planes perpendicular to the tool plane section that are consistent with the possible tool plane section are counted. Alternatively, or additionally, the number of planes perpendicular to the transmission direction of ultrasound radiation emitted by the ultrasound imaging system that include dark regions consistent with the possible tool plane are counted.

This process is repeated for several iterations until the possible tool plane with the maximum number of inliers is identified; this is the actual tool plane. The dark regions that intersect with the tool plane section are tool shadow regions which form an overall tool shadow. Therefore, by identifying the plane that includes the overall tool shadow, the orientation of the tool plane section is determined based on the tool shadow regions.

At 18D, a plane of the volume parallel to the ultrasound beams and containing the determined location of the tip and the full length of the detected overall shadow is calculated and visualized to the user. This section is the tool plane, which contains the full-length needle and the tip. Other views of the needle may also be located based on the position of the tool plane section.

Figure 8A:
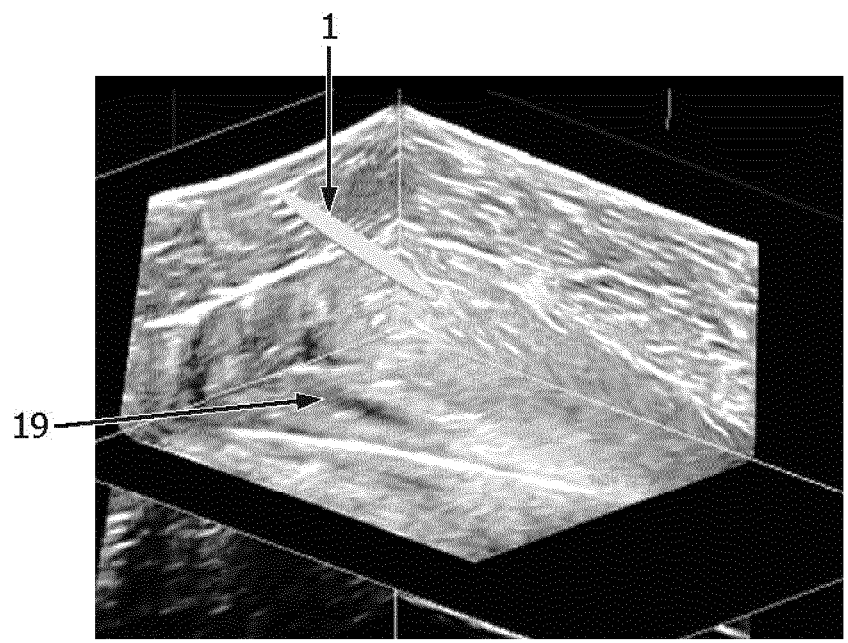
FIG. 8A shows a 3D image of a volume obtained by ultrasound imaging.

FIG. 8A shows an example of a 3D ultrasound image of the interventional tool 1, including the shadow 19 of the interventional device 1 (e.g., needle).

Figure 8B:
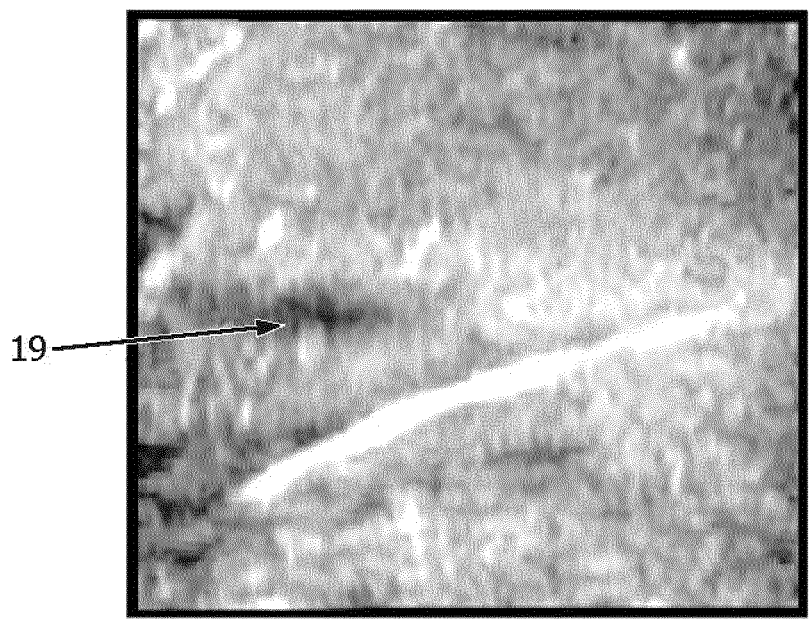
FIG. 8B shows a planar section of the volume of FIG. 4B.

FIG. 8B shows a planar section of the image of FIG. 8A, wherein the planar section is located underneath the needle. The planar section is obtained by the image processor 15, and is subsequently subjected to noise reduction image processing. Dark regions are detected and analyzed to determine whether the dark region represents a shadow of the tool. Also, the planar section is perpendicular to the direction of incident ultrasound beams used to create the image, since planar sections of this orientation provide the most distinctive representation of the tool's shadow 19.

Figure 9:
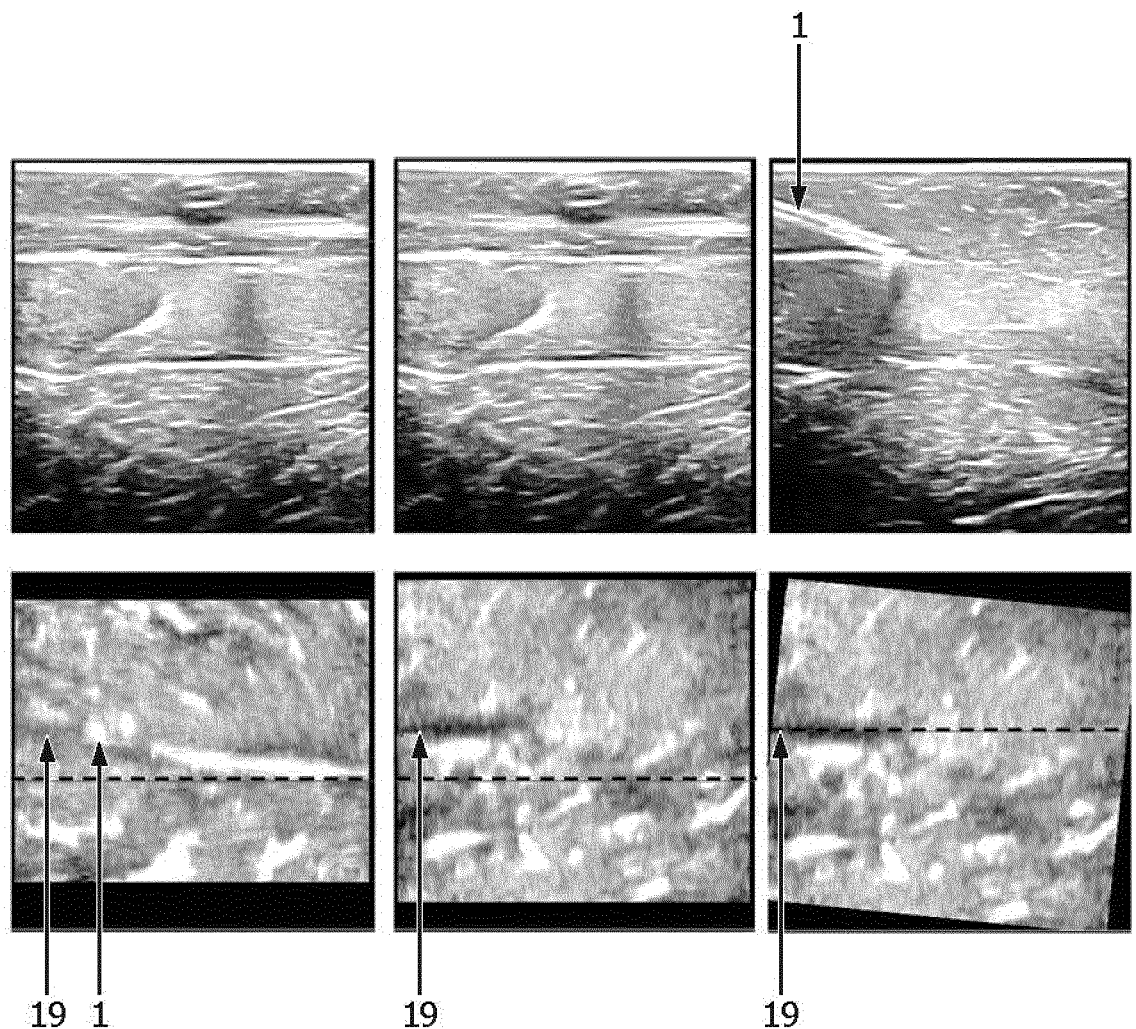
FIG. 9 shows a set of example planar images of a 3D volume, wherein a needle is disposed at a small insertion angle.

FIG. 9 shows an example of a planar section within a 3D image, wherein interventional tool 1 (again, illustratively a needle) is disposed at small angle relative to the transmission direction of ultrasound radiation. The interventional tool 1 has a relative angle of approximately 20° to the face of the transducer. In this case, shadowing is strong but the interventional tool 1 (e.g. a needle) is also still visible. Therefore, both intensity-based and shadowing-based detection techniques result in the correct long-axis needle plane. Therefore, either technique can be used to detect the needle.

The pair of images on the left hand side are cross sections of the 3D volume, wherein the top image is a cross section parallel to the direction of propagation of the ultrasound beam and the lower image is a cross section perpendicular to the direction of propagation of the ultrasound beam. The dotted line in the lower image show the cross sectional plane of the upper image. In the lower image, a small section of the interventional tool 1 is visible as two bright circles. The circles represent the intersection of the plane with the lower wall and upper wall of the interventional tool 1. A small part of the shadow 19 is also visible. Neither the interventional tool 1 nor the shadow of the interventional tool 1 is visible in the upper image, since the upper image is of a cross section of the 3D volume that does not intersect with the interventional tool 1 or the shadow of the interventional tool 1 (as shown by the separation between the dotted line and the interventional tool/shadow in the lower image).
interventional tool 1. The shadow 19 of the interventional tool is shown. The top image is again a cross section parallel to the ultrasound beam. The dotted line in the lower image again shows the cross sectional plane of the upper image. Thus, the upper image is again a cross section of the 3D volume that does not intersect with the interventional tool 1; the cross section is located far from the interventional tool 1. Note that the position of the dotted line is the same for both the left and central lower images. Thus, the left and central upper images are the same.

The pair of images on the right hand side show the detected interventional tool section plane. The top image is a cross section parallel to the ultrasound beam and the lower image is a cross section perpendicular to the ultrasound beam.

The upper image cross section is rotated so that the interventional tool 1 lies fully in the plane. This can be seen from the lower image, in which the dotted line passes along the shadow 19 of the interventional tool 1. This is why the image is rotated clockwise compared to the other two images. In the top right image, the interventional tool 1 is fully in the plane of the image. This is made possible by controlling the rotational angle of the vertical slice (i.e. the slice parallel to the propagation direction).

Thus, the "tool plane section" is a plane which includes the tip of the tool as well as both: a vector parallel to the direction of propagation of the ultrasound radiation and a vector parallel to the elongate axis of the tool. The tool plane section intersects the tool. A plane can always be defined with which these two 2-dimensional vectors intersect. Thus, by controlling the position and rotation of the imaging plane—about an axis parallel to the direction of propagation—a "tool plane section" can be formed in which the general axial direction of the tool is located. A interventional tool (e.g. a needle) can clearly be represented by a two dimensional vector. However, the approach is also applicable to more three dimensional tools which have a general elongate axis. By locating this general elongate axis in the "tool plane section" the tool becomes as visible as possible.

Further, by locating the tool plane section, it is possible to locate other planes that include a section of the interventional tool. Also, based on the location of the tool plane section, a non-planar section of the image that contains the whole tool can be constructed.

Figure 10:
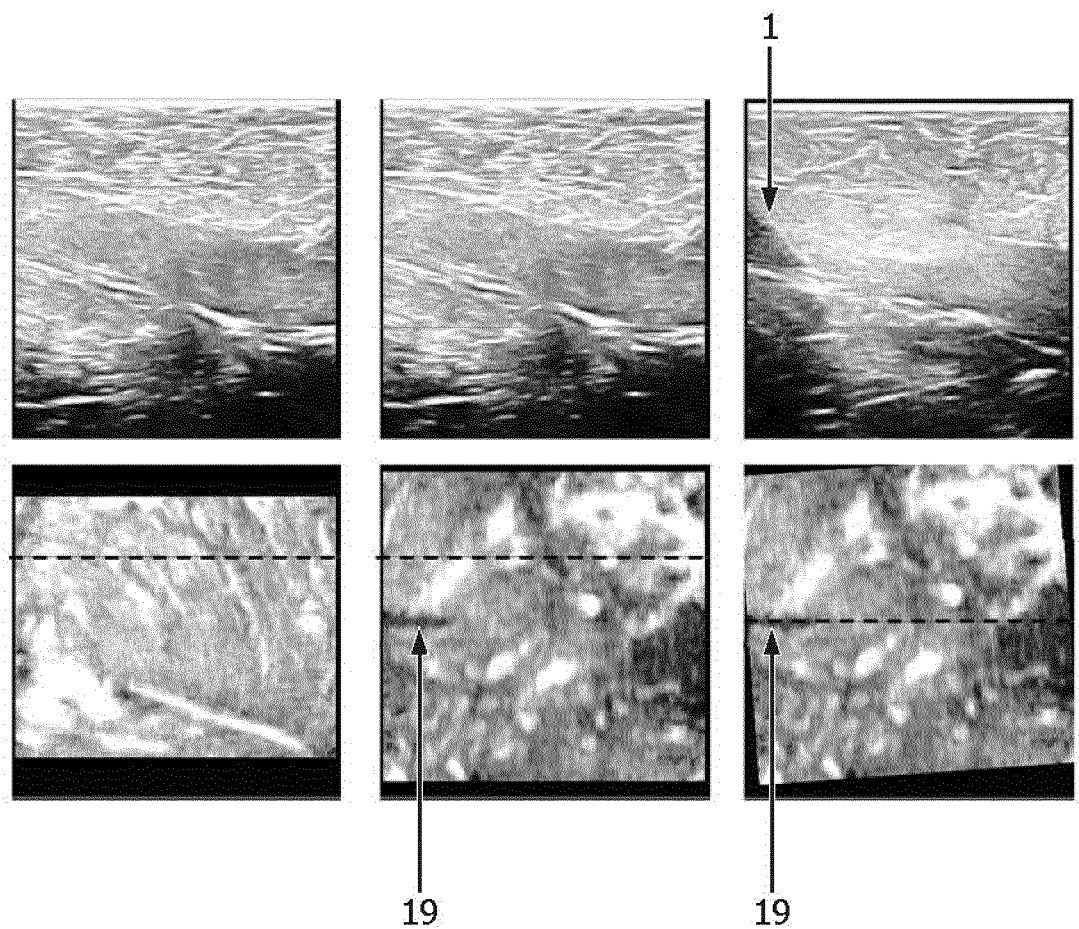
FIG. 10 shows a set of example planar images of a 3D volume, wherein a needle is disposed at a large insertion angle.

FIG. 10 shows an example 2D ultrasound image plane of a 3D volume, wherein a needle is disposed at a large angle relative to the transmission direction of ultrasound radiation; the needle is inserted with a steep angle of approximately 45°. As shown, despite the poor visibility of the needle, the magnitude of the shadow 19 is very strong and can be used to efficiently and accurately locate the tool plane section within the 3D image.

The pair of images on the left hand side are planar sections of the 3D volume. The top image is a cross section parallel to the direction of propagation of the ultrasound beam and the lower image is a cross section perpendicular to the direction of propagation of the ultrasound beam. The lower cross section is located above the needle, which cannot be seen in the image. Note that the bright white line at the bottom right of the left hand lower image represents soft tissue. In clinical ultrasound images of patients, other bright structures such as, bones, fatty structures, nerves and veins can be also present.

The central pair of images are cross sections of the 3D volume. The top image is a cross section parallel to the ultrasound beam and the lower image is a cross section perpendicular to the ultrasound beam. The shadow 19 can now be seen.

The pair of images on the right hand side show the detected needle section plane. The top image is a cross section parallel to the ultrasound beam and the lower image is a cross section perpendicular to the ultrasound beam.

As for the example of FIG. 9, the upper image cross section is positioned and rotated so that the needle lies fully in the plane. This can be seen from the lower image, in which the dotted line passes along the shadow 19 of the interventional tool.

In the top right image, the interventional tool 1 now is visible and fully in the plane of the image. This is made possible by controlling the position and rotational angle of the vertical slice (i.e. the slice parallel to the propagation direction).

Figure 11:
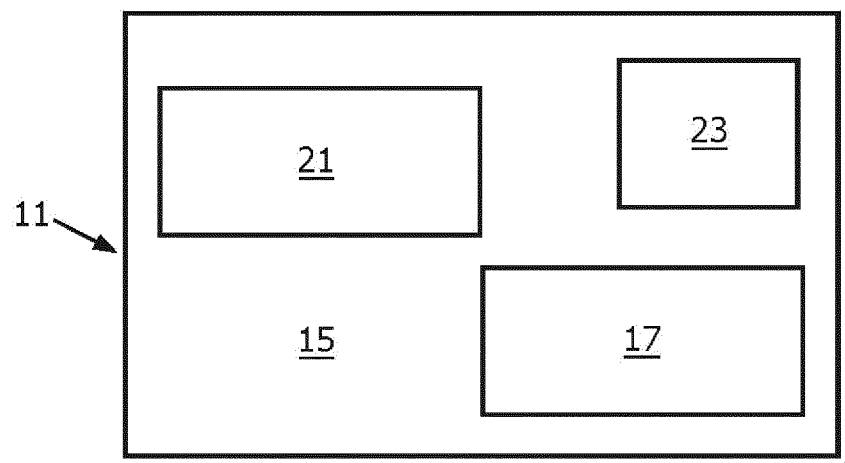
FIG. 11 is a schematic drawing of an apparatus for detecting a tool according to an example.
Figure 12:
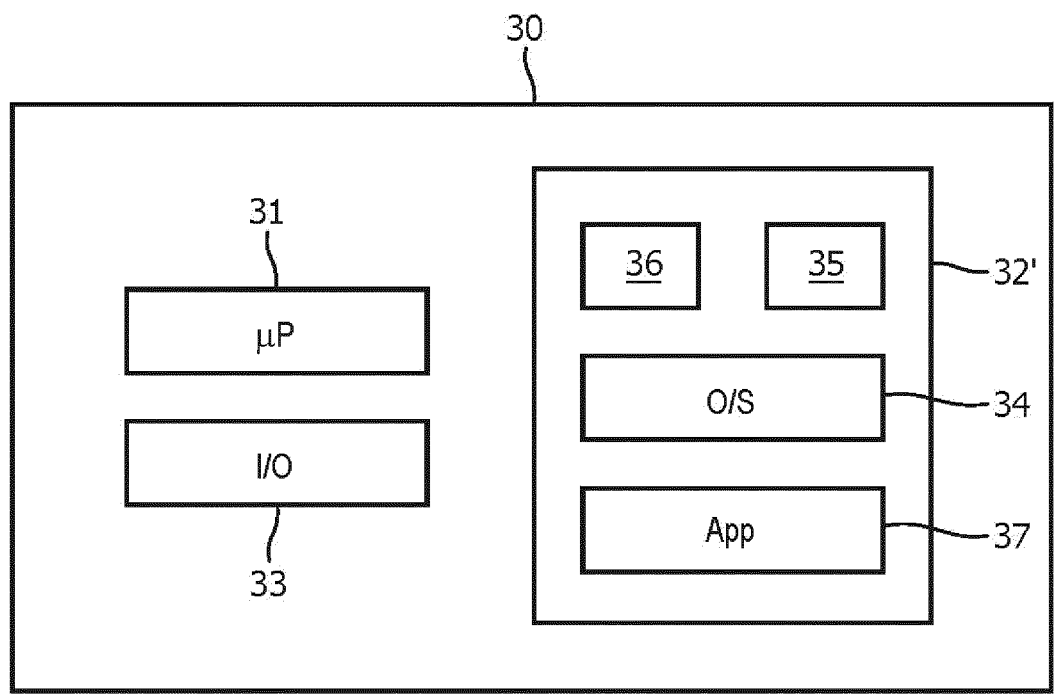
FIG. 12 shows a computer suitable for implementing the processing carried out by the apparatus.

FIG. 11 shows another example of the apparatus 11 as an image processor. In this example, the image processor 15 comprises a second tool detection module 21, which operates in conjunction with the tip tool detection module 17 to efficiently and robustly detect the long-axis needle plane in the 3D ultrasound volume. The second tool detection module 21 is also illustrated in the example of FIG. 2, wherein the second module is arranged to perform the same function as in the example from FIG. 11.

The tip tool detection module inspects the volume for dark regions of the ultrasound images that represent a shadow of the tool. This method is most beneficial in cases of large insertion angles but can also be used to detect a tool at small insertion angles. Therefore, shadow based tool detection is suitable for detecting a tool at any insertion angle.

The second module is adapted to detect the needle based on its 3D appearance when the needle is orientated at a small insertion angle. For example, the second module may be configured to detect the tool using an intensity and frequency based algorithm. Such an algorithm is discussed in H. H. M. Korsten, P. H. N. de With, and J. W. M. Bergmans, "Needle detection in medical image data," 2012, and A. Pourtaherian, S. Zinger, P. H. N. de With, H. H. M. Korsten, and N. Mihajlovic, "Gabor-Based Needle Detection and Tracking in Three-Dimensional Ultrasound Data Volumes," in Proc. IEEE Int. Conf. Image Processing (ICIP), 2014, pp. 3602-6, for example. As mentioned above, shadow based detection can be used to identify a needle for any insertion angle. By providing an apparatus 11 that is capable of tool detection by either method, the tool can be detected with increased robustness to noise and reliability of detection.

The apparatus 11 also includes a controller which is configured to control the tip and second tool detection modules to perform their corresponding tool detection procedures. The controller may be configured to control the image processor to determine whether the tool is visible within ultrasound image data. If the tool is visible, the controller may command the second tool detection unit to perform the second tool detection procedure. In an example, the apparatus includes a display unit for displaying an ultrasound image. Once the image processor has determined the location of the tool plane section, it transmits the image to the display unit to visualize the tool plane section to a user.

The apparatus may be an image processor. Alternatively, in some examples, the apparatus comprises an ultrasound imaging system for generating an ultrasound image and the image processor is configured to communicate with the ultrasound imaging system to receive the ultrasound image data generated by the 3D ultrasound imaging system and perform the tip tool detection procedure on the received data.

The apparatus may be suitable for use with any type of tool that can be imaged by ultrasound radiation. For example, a metal tool or a tool with a reflective coating. The tool may be a needle, a catheter, an electrode or a laparoscope, for example. The angular range over which visibility of the tool may depend on the type of tool.

As mentioned above, the image processing may be implemented by a controller. The controller may comprise a computer 30, as shown in FIG. 8.

The computer 30 includes, but is not limited to, PCs, workstations, laptops, PDAs, palm devices, servers, storages, and the like. Generally, in terms of hardware architecture, the computer 30 may include one or more processors 31, memory 32, and one or more I/O devices 33 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 31 is a hardware device for executing software that can be stored in the memory 32. The processor 31 can be virtually any custom made or commercially available processor, a central processing unit (CPU), a digital signal processor (DSP), or an auxiliary processor among several processors associated with the computer 30, and the processor 31 may be a semiconductor based microprocessor (in the form of a microchip) or a microprocessor.

The memory 32 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 32 may incorporate electronic, magnetic, optical, and/or other types of storage media. Note that the memory 32 can have a distributed architecture, where various components are situated remote from one another, but can be accessed by the processor 31.

The software in the memory 32' may include one or more separate programs, each of which comprises an ordered listing of executable instructions for implementing logical functions. The software in the memory 32 includes a suitable operating system (O/S) 34, compiler 35, source code 36, and one or more applications 37 in accordance with exemplary embodiments.

The application 37 comprises numerous functional components such as computational units, logic, functional units, processes, operations, virtual entities, and/or modules.

The operating system 34 controls the execution of computer programs, and provides scheduling, input-output control, file and data management, memory management, and communication control and related services.

Application 37 may be a source program, executable program (object code), script, or any other entity comprising a set of instructions to be performed. When a source program, then the program is usually translated via a compiler (such as the compiler 350), assembler, interpreter, or the like, which may or may not be included within the memory 320, so as to operate properly in connection with the operating system 340. Furthermore, the application 37 can be written as an object oriented programming language, which has classes of data and methods, or a procedure programming language, which has routines, subroutines, and/or functions, for example but not limited to, C, C++, C #, Pascal, BASIC, API calls, HTML, XHTML, XML, ASP scripts, JavaScript, FORTRAN, COBOL, Perl, Java, ADA, .NET, and the like.

The I/O devices 33 may include input devices such as, for example but not limited to, a mouse, keyboard, scanner, microphone, camera, etc. Furthermore, the I/O devices 33 may also include output devices, for example but not limited to a printer, display, etc. Finally, the I/O devices 33 may further include devices that communicate both inputs and outputs, for instance but not limited to, a network interface controller (NIC) or modulator/demodulator (for accessing remote devices, other files, devices, systems, or a network), a radio frequency (RF) or other transceiver, a telephonic interface, a bridge, a router, etc. The I/O devices 33 also include components for communicating over various networks, such as the Internet or intranet.

When the computer 30 is in operation, the processor 31 is configured to execute software stored within the memory 32, to communicate data to and from the memory 32, and to generally control operations of the computer 30 pursuant to the software. The application 37 and the operating system 34 are read, in whole or in part, by the processor 31, perhaps buffered within the processor 310, and then executed.

When the application 37 is implemented in software it should be noted that the application 37 can be stored on virtually any computer readable medium for use by or in connection with any computer related system or method. In the context of this document, a computer readable medium may be an electronic, magnetic, optical, or other physical device or means that can contain or store a computer program.

The invention claimed is:

1. An apparatus for detecting a location of a tool including a tip of the tool in a volumetric region, said apparatus comprising:
    an image processor adapted to receive from an ultrasound array an ultrasound image data of the volumetric region, said image processor coupled to a memory that stores instructions, which when executed by the image processor, cause the image processor to:
    reconstruct from the ultrasound image data a first ultrasound image having a first tool shadow region, wherein the first ultrasound image corresponds to a first steering angle of an ultrasound beam with respect to a surface of the ultrasound array, and a second ultrasound image having a second tool shadow region, wherein the second ultrasound image corresponds to a second steering angle of the ultrasound beam being different from the first steering angle;
    identify a first differential shadow region (ACB) within the volumetric region based on a relative difference between the first tool shadow region and the second tool shadow region; and
    determine based on the first differential shadow region the location of the tip of the tool.

2. The apparatus of claim 1, wherein the instructions, when executed by the image processor, further cause the image processor to:
    reconstruct a third ultrasound image having a third tool shadow region, wherein the third ultrasound image corresponds to a third steering angle of the ultrasound beam being different from the second steering angle,
    identify a second differential shadow region within the volumetric region based on the relative difference between the third too shadow region and either of the first and the second tool shadow regions; and
    correlate the first differential shadow region with the second differential shadow region, wherein a further determination of the location of the tip of the tool is based on the correlation of the first and second differential shadow regions.

3. The apparatus of claim 1, wherein instructions, when executed by the image processor, further cause the image processor to: identify the first differential shadow region in a subtracted image obtained by subtracting intensities of the respective pixels from the first and the second ultrasound images.

4. The apparatus of claim 3, wherein the first differential shadow region in the subtracted image includes image pixels having intensities values above a threshold intensity value.

5. The apparatus of claim 3, wherein the first differential shadow region within the subtracted image includes image pixels having intensities values below a threshold intensity value.

6. The apparatus of claim 2, wherein the received ultrasound image data comprise a 3D ultrasound image data of the volumetric region.

7. The apparatus of claim 6, wherein the first ultrasound image, the second ultrasound image and the third ultrasound image belong to a plurality of image planes forming a 3D ultrasound image of the volumetric region.

8. The apparatus of claim 6, wherein the instructions, when executed by the image processor, further cause the image processor to: determine the location of a tool plane section within the 3D ultrasound image data based on the determined location of the tip of the tool, wherein the tool plane section represents a plane within a 3D ultrasound image of the volumetric region, in which an entire length of the tool is present.

9. The apparatus of claim 8, wherein the instructions, when executed by the image processor, further cause the image processor to: reconstruct a short-axis plane including a short-axis of the tool and the determined location of the tip of the tool.

10. The apparatus of claim 7, wherein instructions, when executed by the image processor, further cause the image processor to: identify a plurality of tool shadow regions by detecting dark regions present in the plurality of image planes and determining whether the dark regions correspond to a shadow of the tool, wherein the first, the second and the third tool shadow regions belong to the plurality of tool shadow regions.

11. The apparatus of claim 2, wherein the ultrasound image data comprise a plurality of 3D ultrasound image frames, and wherein each of the first ultrasound image, the second ultrasound image and the third ultrasound image is reconstructed from a different 3D ultrasound frame from said plurality of 3D ultrasound frames.

12. The apparatus of claim 2, wherein the ultrasound image data comprise a plurality of 2D ultrasound image planes, and wherein each of the first ultrasound image, the second ultrasound image and the third ultrasound image is reconstructed from a different 2D ultrasound image from said plurality of 2D ultrasound image planes.

13. The apparatus of claim 1, wherein the instructions, when executed by the image processor, further cause the image processor to:
    to perform a second tool detection procedure which comprises:
    detect the tool based on a representation of the tool in the ultrasound image, preferably using an intensity and/or frequency based algorithm.

14. An ultrasound system comprising:
    an apparatus of claim 1; and
    an ultrasound array arranged to steer the ultrasound beam towards the volumetric region and provide the ultrasound image data to the image processor.

15. The apparatus of claim 8 further comprising a display for displaying an ultrasound image, wherein the image processor is configured to transmit an image of the tip of the tool plane and/or the tool plane section to the display.

16. A method for detecting a tool including a tip of the tool in a volumetric region, comprising:
    obtaining an ultrasound image data of the volumetric region;
reconstructing from the ultrasound image data a first ultrasound image having a first tool shadow region, wherein the first ultrasound image corresponds to a first steering angle of an ultrasound beam with respect to a surface of an ultrasound array, and a second ultrasound image having a second tool shadow region, wherein the second ultrasound image corresponds to a second steering angle of the ultrasound beam being different from the first steering angle;
    identifying a differential shadow region (ACB) within the volumetric region based on a relative difference between the first tool shadow region and the second tool shadow region; and
    determining based on the differential shadow region a location of the tip of the tool.

17. The method of claim 16, wherein identifying the differential shadow region comprises subtracting intensities of the respective pixels from the first and the second ultrasound images thereby obtaining a subtracted image.

18. The method of claim 16, wherein the obtained ultrasound image data of the volumetric region is a 3D ultrasound image; and the method further comprises
    determining a location of a tool plane section within the 3D ultrasound image based on the determined location of the tip of the tool, wherein the tool plane section represents a plane within the 3D ultrasound image in which an entire length of the tool is present.

19. A tangible non-transitory computer readable medium that stores instructions, which when executed by a processor, cause the processor to:
    obtain an ultrasound image data of a volumetric region;
    reconstruct from the ultrasound image data a first ultrasound image having a first tool shadow region, wherein the first ultrasound image corresponds to a first steering angle of an ultrasound beam with respect to a surface of an ultrasound array, and a second ultrasound image having a second tool shadow region, wherein the second ultrasound image corresponds to a second steering angle of the ultrasound beam being different from the first steering angle;
    identify a differential shadow region (ACB) within the volumetric region based on a relative difference between the first tool shadow region and the second tool shadow region; and
    determine based on the differential shadow region a location of a tip of a tool.

20. The tangible non-transitory computer readable medium of claim 19, wherein the instructions, which when executed by the processor, further cause the processor to:
    identify the differential shadow region comprises subtracting intensities of the respective pixels from the first and the second ultrasound images thereby obtaining a subtracted image.

21. The tangible non-transitory computer readable medium of claim 19, wherein the obtained ultrasound image data of the volumetric region is a 3D ultrasound image; and the instructions, when executed by the processor further cause the processor to:
    determine a location of a tool plane section within the 3D ultrasound image based on the determined location of the tip of the tool, wherein the tool plane section represents a plane within the 3D ultrasound image in which an entire length of the tool is present.

* * * * *